(12) United States Patent
Kang

(10) Patent No.: US 9,383,569 B2
(45) Date of Patent: Jul. 5, 2016

(54) MAGNIFICATION OBSERVATION DEVICE

(71) Applicant: Keyence Corporation, Osaka (JP)

(72) Inventor: Woobum Kang, Osaka (JP)

(73) Assignee: Keyence Corporation, Osaka (JP)

( * ) Notice: Subject to any disclaimer, the term of this patent is extended or adjusted under 35 U.S.C. 154(b) by 689 days.

(21) Appl. No.: 13/648,571

(22) Filed: Oct. 10, 2012

(65) Prior Publication Data

US 2013/0093872 A1 Apr. 18, 2013

(30) Foreign Application Priority Data

Oct. 14, 2011 (JP) ................ 2011-227395

(51) Int. Cl.
*G02B 21/36* (2006.01)
*G02B 21/24* (2006.01)
*H04N 5/232* (2006.01)
*G01N 21/64* (2006.01)

(52) U.S. Cl.
CPC ............ G02B 21/244 (2013.01); G02B 21/365 (2013.01); H04N 5/23212 (2013.01); *G01N 21/6458* (2013.01)

(58) Field of Classification Search
CPC .................................................... G02B 21/244
USPC .......................................................... 348/79
See application file for complete search history.

(56) References Cited

U.S. PATENT DOCUMENTS

| | | | | |
|---|---|---|---|---|
| 2003/0214706 A1* | 11/2003 | Maddison | | 359/368 |
| 2005/0175233 A1* | 8/2005 | Yoneyama | | G01N 21/9501 382/145 |
| 2010/0149362 A1 | 6/2010 | Kang | | |
| 2010/0149363 A1 | 6/2010 | Inomata et al. | | |
| 2010/0149364 A1 | 6/2010 | Kang | | |
| 2011/0133066 A1* | 6/2011 | Nozoe | | H01J 37/265 250/252.1 |

FOREIGN PATENT DOCUMENTS

| | | |
|---|---|---|
| JP | H08-190045 A | 7/1996 |
| JP | 2002-350320 A | 12/2002 |
| JP | 2004-158392 A | 6/2004 |
| JP | 2005-037902 A | 2/2005 |
| JP | 2006-023476 A | 1/2006 |
| JP | 2007-310231 A | 11/2007 |
| JP | 2008-139794 A | 6/2008 |
| JP | 2008-139795 A | 6/2008 |
| JP | 2010-130408 A | 6/2010 |
| JP | 2010-141697 A | 6/2010 |
| JP | 2010-141700 A | 6/2010 |
| JP | 2012-150335 A | 8/2012 |

* cited by examiner

*Primary Examiner* — Tung Vo
*Assistant Examiner* — Rowina Cattungal
(74) *Attorney, Agent, or Firm* — Kilyk & Bowersox, P.L.L.C.

(57) ABSTRACT

Provided is a magnification observation device in which a focus of the imaging unit can be focused on the observation surface of the object in observation object region in a short period of time. An unit region of an observation object is imaged at a plurality of Z-positions by moving a object lens in the light-axis direction, the plurality of pieces of image data corresponding to the unit region are captured. An image of the observation object is displayed in the display unit as a navigation image. Shape data which indicates the position of the surface of the observation object in the unit region is generated. An observation object region on observation object is designated based on the navigation image. Based on the generated shape data, a focus of the object lens is on the surface of the observation object on the observation object region designated.

14 Claims, 13 Drawing Sheets

MAGNIFICATION OBSERVATION DEVICE

CROSS-REFERENCE TO RELATED APPLICATIONS

The present application claims foreign priority based on Japanese Patent Application No. 2011-227395, filed Oct. 14, 2011, the contents of which is incorporated herein by reference.

BACKGROUND OF THE INVENTION

1. Field of the Invention

The present invention relates to a magnification observation device which images an object to display an image of the object.

2. Description of Related Art

Japanese Patent Publication No. 2007-310231 discloses a microscope devise which has a macro image acquiring unit and a micro image acquiring unit. In this microscope device, the macro image acquiring unit is used to capture the macro image which is low magnification image of a sample, and the micro image acquiring unit is used to capture the micro image which is high magnification image of a sample.

At the time of acquiring the macro image and micro image, first, the macro image which includes the entire sample is captured by the macro image acquiring unit. With reference to the macro image captured, imaging condition for acquiring the micro image is set.

Acquisition range is set as imaging condition for acquiring the micro image. Also, focus measurement position is set as imaging condition for acquiring the micro image. Focus measurement is performed at the focus measurement position set, by using a micro imaging device.

In the above focus measurement, for example, with the object lens which the micro image acquiring unit includes is moved relative to the sample, a focus of the object lens is focused at focus measurement position, and the relative distance between the object lens and the sample is determined at the time when a focus of the object lens is focused at focus measurement position.

The higher magnification of the object lens is, the smaller focus depth of the object lens is. Therefore, in the micro image acquiring unit having the object lens of high magnification, at the time of focus measurement, it is needed to search in small pitch over a wide range whether or not a focus of the object lens is at the focus measurement position. In this case, it takes a long time for the focus measurement.

SUMMARY OF THE INVENTION

The present invention provides a magnification observation device in which a focus of the imaging unit can be focused on the observation surface of the object in observation object region in a short period of time.

(1) According to one embodiment of the invention, there is provided a magnification observation device which images an object to display an image of the object, the device including: a placement unit (or holder) where the object is mounted; an imaging unit (or an imaging portion or component or imaging operation) for imaging the object mounted on the placement unit to capture (acquire) a first image data for displaying an image of the object; a display unit that displays an image of the object as a region presentation image based on the first image data captured (acquired) by the imaging unit; a processing unit (or processing portion or component or processing operation) that generates focus position data indicating the position of observation surface of the object in the light-axis direction of the imaging unit, based on the first image data captured (acquired) by the imaging unit; an operation unit (or operation portion or component) that is operated by a user for designating a region of the object to be observed as an observation object region in the region presentation image displayed by the display unit; and a control unit (or control portion or control component or controlling operation) that performs a focusing operation controlling at least one of the imaging unit and the placement unit so that a focus of the imaging unit is on the observation surface in the observation object region designated by the operation of the operation unit, based on the focus position data generated by the processing unit.

In the magnification observation device, an object mounted on the placement unit is imaged by the imaging unit, and a first image data is captured. An image of the object is displayed on the display unit as a region presentation image based on the first image data captured. Also, focus position data is generated by the processing unit based on the first image data captured.

In this case where an observation object region is designated in the region presentation image by the operation unit, a focusing operation is performed based on the focus position data which is generated by the processing unit, a focus of the imaging unit is on the observation surface in the observation object region designated.

In this case, as the focus position data indicates the position of the observation surface of the object in the light-axis direction, it can result in reduction in time for performing a focusing operation. Consequently, the focusing operation in which a focus of the imaging unit is focused on the observation surface of the observation object region of the object can be performed in a short period of time.

(2) The focusing operation may include parameter setting operation that sets a position parameter related to positional relationship between the imaging unit and the placement unit in the light-axis direction of the imaging unit, based on the focus position data generated by the processing unit, and a moving operation that moves at least one of the imaging unit and the placement unit along the light-axis direction of the imaging unit based on the position parameter set by the parameter setting operation.

In the time of the focusing operation, first, a position parameter related to positional relationship between the imaging unit and the placement unit in the light-axis direction of the imaging unit is set, based on the focus position data generated by the processing unit. Subsequently, at least one of the imaging unit and the placement unit is moved along the light-axis direction of the imaging unit based on the position parameter set.

In this case, as the focus position data indicates the position of the observation surface of the object in the light-axis direction of the imaging unit, a first parameter can be set in a short period of time.

(3) The operation unit that may be configured to allow a user to designate a plurality of unit regions (piece regions) as the observation object region in the region presentation image, and the control unit that may be configured so as to perform the focusing operation on each of the plurality of unit regions designated by the operation unit, based on the focus position data generated by the processing unit.

In this case, even if the desired observation object region is larger than the unit region, a user can designate the observation object region on the region presentation image. Also, as the focusing operation based on the focus position data on each of the plurality of unit regions designated is repeated, the focus of the imaging unit can be focused on the observation surface of the plurality of unit regions in a short period of time.

(4) The control unit that may control the imaging unit so as to capture a second image data for displaying an image of the observation object region by imaging the observation object region after the focus of the imaging unit has been on the observation surface in the observation object region by the focusing operation, the display unit that may display an image of the observation object region based on the second image data captured by the imaging unit, the imaging unit that may image an object with a first imaging condition at the case of acquiring the first image data and images an object with a second imaging condition at the case of acquiring the second image data, and the first imaging condition and the second imaging condition may be set so that the quality of an image based on the first image data is lower than that of an image based on the second image data.

In this case, as there is no need to equal the quality of an image based on the first image data and the quality of an image based on the second image data, the time for imaging an object with the first imaging condition can be reduced compared to the time for imaging an object with the second condition. Therefore, the region presentation image is displayed on the display unit in a short period of time.

(5) The control unit that may control the imaging unit so as to sequentially image a plurality of unit regions, to thereby capture the first image data with respect to each unit region, at the time of imaging one unit region of the plurality of unit region for acquiring the first image data, the control unit that may control the processing unit so as to generate the focus position data in the one unit region in the light-axis direction of the imaging unit based on the first image data captured by imaging of the one unit region, and at the time of imaging the one unit region and subsequent unit regions, the imaging unit may capture the first image data using the focus position data generated at the time of imaging of the one unit region.

In this case, as the focus position data indicates the position of the observation surface of the object in the light-axis direction, the imaging condition to image the one unit region and subsequent unit regions can be set appropriately based on the focus position data corresponding to one unit region. Therefore, the one unit region and subsequent unit regions can be imaged with appropriate imaging condition, to thereby be captured the first image data.

(6) The control unit that may control at least one of the imaging unit and the placement unit so that a focus of the imaging unit is moved to a plurality of positions in the light-axis direction of the imaging unit and the object is respectively imaged at the plurality of positions, to thereby may capture a plurality of pieces of first image data, the operation unit that may be configured to allow a user to select at least part of the plurality of pieces of first image data captured respectively corresponding to the plurality of positions, and the control unit that may display an image of the object as a region presentation image in the display unit based on the at least part of the first image data selected by the operation unit.

A plurality of images that are displayed based on the plurality of pieces of first image data are focused on different units or are different in focal degree. Therefore the user can display a desired image, out of the plurality of images being focused on different units of different in focal degree, as the region presentation image in the display unit. This allows the user to appropriately designate the observation object region.

(7) The control unit that may control at least one of the imaging unit and the placement unit so that a focus of the imaging unit is moved to a plurality of positions in the light-axis direction of the imaging unit and the object is respectively imaged at the plurality of positions, to thereby may capture a plurality of pieces of first image data, and may display an image focused on the plurality of positions of the observation surfaces of the object as a region presentation image in the display unit by selectively using each part of the plurality of pieces of the first image data captured.

In this case, an image respectively focused on the plurality of positions of the observation surfaces of the object is displayed as a region presentation image. Thereby, this allows the user to appropriately designate the observation object region.

Provided is a magnification observation device in which a focus of the imaging unit can be focused on the observation surface of the object in observation object region in a short period of time

DETAILED DESCRIPTION OF PREFERRED EMBODIMENTS

A magnification observation device according to one embodiment of the present invention will be described with reference to the drawings.

(1) Configuration of Magnification Observation Device

Figure 1:
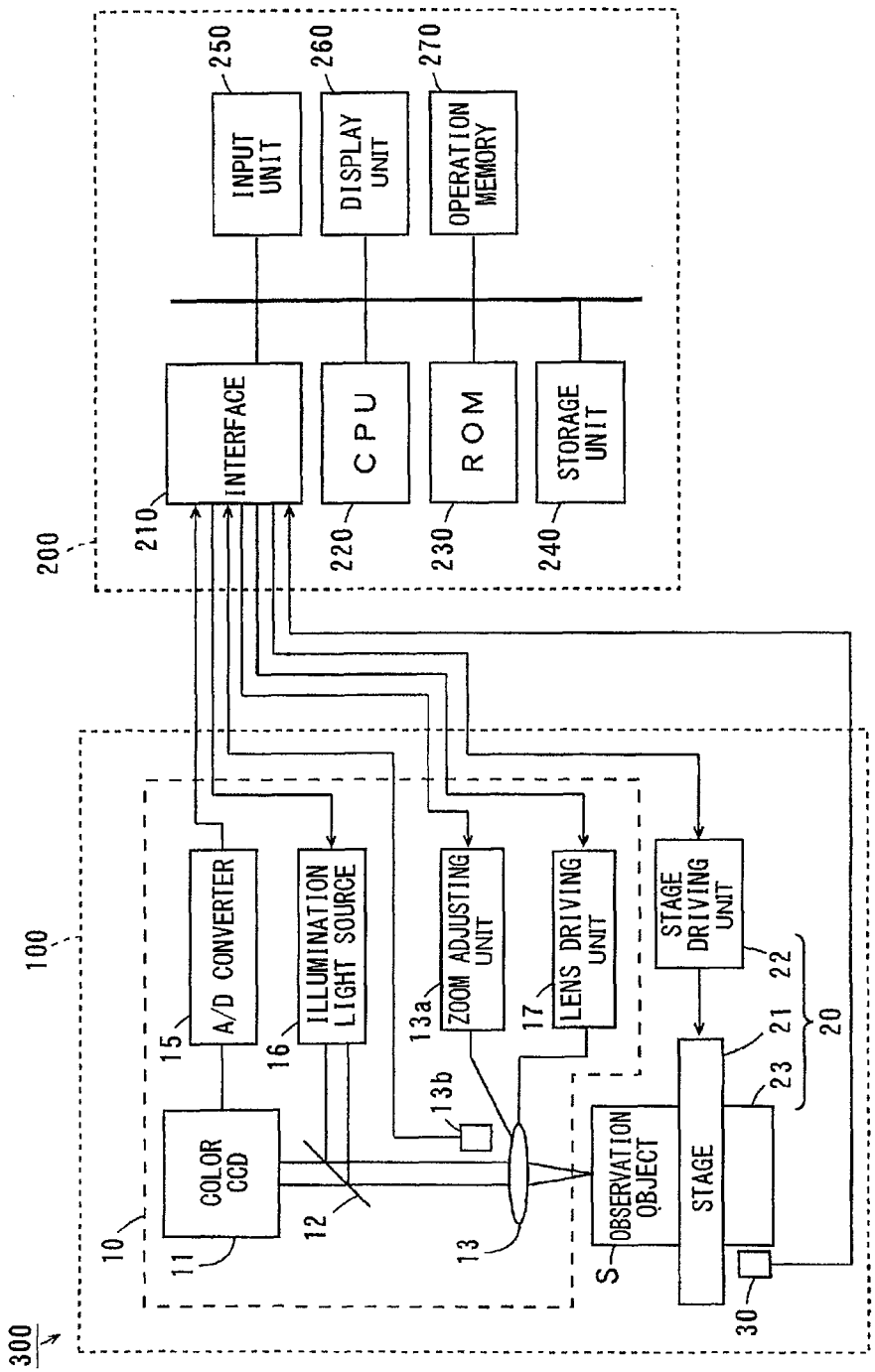
FIG. 1 is a block diagram showing a configuration of a magnification observation device according to one embodiment of the present invention.

FIG. 1 is a block diagram showing a configuration of a magnification observation device according to one embodiment of the present invention.

Hereinafter, two directions orthogonal within a horizontal plane are taken as an X-direction and a Y-direction, and a vertical direction (perpendicular direction) to the X-direction and the Y-direction is taken as a Z-direction.

As shown in FIG. 1, a magnification observation device 300 is provided with a microscope 100 and an image processing apparatus 200.

The microscope 100 includes an imaging unit 10, a stage unit 20, and a rotational angle sensor 30. The imaging unit 10 includes a color CCD (charge coupled device) 11, a half mirror 12, an object lens 13, a zoom adjusting unit 13a, a magnification detecting unit 13b, an A/D converter (analog/digital converter) 15, an illumination light source 16, and a lens driving unit 17. The stage unit 20 includes a stage 21, a stage driving unit 22, and a stage supporting unit 23. An observation object S is mounted on the stage 21.

The illumination light source 16 is, for example, a halogen lamp or a white LED (light-emitting diode) which generates white light. White light generated by the illumination light source 16 is reflected by the half mirror 12, and thereafter collected by the object lens 13 onto the observation object S on the stage 21.

The white light reflected by the observation object S is transmitted through the object lens 13 and the half mirror 12, and incident on the color CCD 11. The color CCD 11 has a plurality of pixels. Each pixel is configured of three kinds of sub-pixels that respectively receive red wavelength light, green wavelength light, and blue wavelength light. The plurality of pixels are two-dimensionally arrayed at a fixed pixel pitch (distance between centers of mutually adjacent two pixels). From each of the pixels in the color CCD 11, an electric signal corresponding to a light receiving amount is outputted. The output signal of the color CCD 11 is converted to the digital signal by the A/D converter 15. The digital signal outputted from the A/D converter 15 is sequentially provided as image data including a plurality of pieces of pixel data to the image processing apparatus 200. Instead of the color CCD 11, an imaging element such as a CMOS (complementary metal oxide semiconductor) image sensor may be used.

In the present embodiment, the object lens 13 is a zoom lens. The zoom adjusting unit 13a changes a magnification of the object lens 13 by control of the image processing apparatus 200. The magnification detecting unit 13b detects the magnification of the object lens 13, and provides a detection result to the image processing apparatus 200. Thereby, the magnification of the object lens 13 is adjustable by the image processing apparatus 200 to an arbitrary magnification within a fixed range. It is to be noted that the zoom adjusting unit 13a may be operated by the user, to adjust the magnification of the object lens 13. In this case, the adjusted magnification of the object lens 13 is detected by the magnification detecting unit 13b, and provided to the image processing apparatus 200.

Further, the object lens 13 is provided movably in the Z-direction. The lens driving unit 17 moves the object lens 13 in the Z-direction by control of the image processing apparatus 200. Thereby, a focal position of the imaging unit 10 moves in the Z-direction.

The stage 21 is rotatably provided on the stage supporting unit 23 around an axis in the Z direction. The stage driving unit 22 moves the stage 21 in an x-direction and a y-direction, described later, relatively with respect to the stage supporting unit 23 based on a movement command signal (drive pulse) provided from the image processing apparatus 200. The stage driving unit 22 uses a stepping motor. The rotational angle sensor 30 detects a rotational angle of the stage 21, and provides the image processing apparatus 200 with an angle detection signal indicating the detected angle. In the image processing apparatus 200, based on the response signal from the stage driving unit 22 with respect to the movement command signal and the angle detection signal from the rotational angle sensor 30, a position of the stage 21 in the X-direction and the Y-direction and a rotational angle thereof are acquired.

The image processing apparatus 200 includes an interface 210, a CPU (central processing unit) 220, a ROM (read only memory) 230, a storage unit 240, an input unit 250, a display unit 260, and an operation memory 270.

A system program is stored into the ROM 230. The storage unit 240 is made up of a hard disk and the like. In the storage unit 240, a later-described magnification observation program is stored, and a variety of data such as image data provided from the microscope 100 through the interface 210 are also stored. A detail of the magnification observation program will be described later. The input unit 250 includes a keyboard and a pointing device. As the pointing device, a mouse, a touch pad, a joystick, or the like is used. The input unit 250 may be a touch pad.

The display unit 260 is configured, for example, of a liquid crystal display panel or an organic EL (electroluminescent) panel.

The operation memory 270 is made up of a RAM (random access memory), and used for processing a variety of data.

The CPU 220 executes the magnification observation program stored in the storage unit 240, to perform the magnification observation process based on image data by means of the operation memory 270, and also displays an image based on the image data in the display unit 260. Further, the CPU 220 controls the color CCD 11, the zoom adjusting unit 13a, the illumination light source 16, the lens driving unit 17, and the stage driving unit 22 of the microscope 100 through the interface 210.

Figure 2:
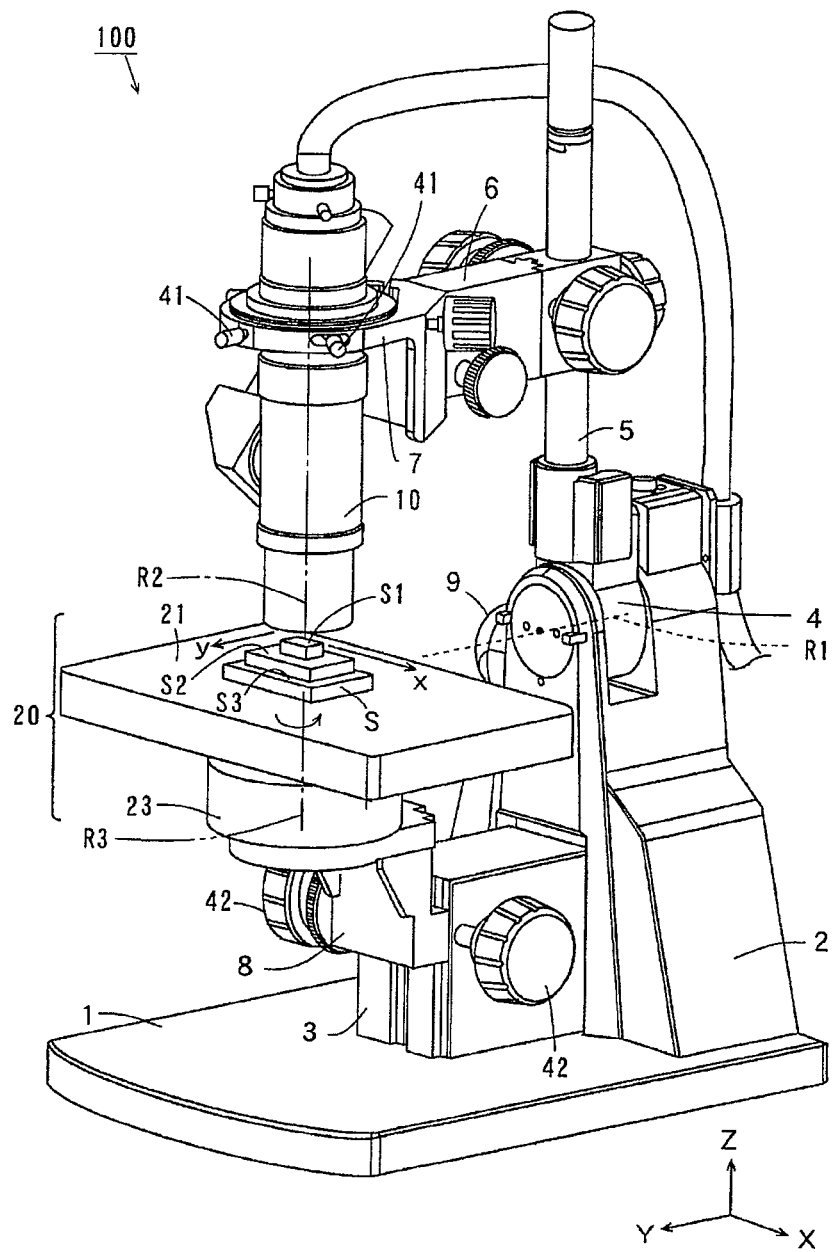
FIG. 2 is a perspective view showing a microscope of the magnification observation device according to one embodiment of the present invention.

FIG. 2 is a perspective view showing the microscope 100 of the magnification observation device 300 according to one embodiment of the present invention. In FIG. 2, the X-direction, the Y-direction, and the Z-direction are indicated by arrows.

As shown in FIG. 2, the microscope 100 has a base 1. A first supporting base 2 is attached onto the base 1, and a second supporting base 3 is also attached to the front surface of the first supporting base 2 so as to be embedded thereinto.

A connecting unit 4 is rotatably attached to the top edge of the first supporting base 2 around a rotational axis R1 extending in the Y-direction. A rotational column 5 is attached to the connecting unit 4. Thereby, the rotational column 5 is inclinable within a vertical plane parallel to the Z-direction with the rotational axis R1 taken as a fulcrum point in association with rotation of the connecting unit 4. The user can fix the connecting unit 4 to the first supporting base 2 by means of a fixing knob 9.

A circular supporting unit 7 is attached to the front surface of a connecting unit 6. A substantially tubular imaging unit 10 is attached to the supporting unit 7. In the state of FIG. 2, a light axis R2 of the imaging unit 10 is parallel to the Z-direction. The supporting unit 7 has a plurality of adjustment screws 41 for moving the imaging unit 10 within the horizontal plane. It is possible to adjust a position of the imaging unit 10 so that the light axis R2 of the imaging unit 10 vertically intersects with a rotational axis R1 by means of the plurality of adjustment screws 41.

A slider 8 is attached, slidably in the Z-direction, to the front surface of the second supporting base 3 on the base 1. An adjustment knob 42 is provided on the side surface of the second supporting base 3. A position of the slider 8 in the Z-direction (height direction) is adjustable by an adjustment knob 42.

The stage supporting unit 23 of the stage unit 20 is attached onto the slider 8. The stage 21 is rotationally provided around a rotational axis R3 in the Z-direction with respect to the stage supporting unit 23. Further, the x-direction and the y-direction intersecting with each other within the horizontal plane are set on the stage 21. The stage 21 is provided movably in the x-direction and the y-direction by the stage driving unit 22 of FIG. 1. When the stage 21 rotates around the rotational axis R3, the x-direction and the y-direction of the stage 21 also rotate. This leads to inclination of the x-direction and the y-direction of the stage 21 within the horizontal plane with respect to the X-direction and the Y-direction.

An imaging range (visual field range) of the imaging unit 10 varies depending on a magnification of the imaging unit 10. Hereinafter, the imaging range of the imaging unit 10 is referred to as a unit region. The stage 21 can be moved in the x-direction and the y-direction, to thereby capture image data of a plurality of unit regions. The image data of the plurality of unit regions can be connected, to thereby display images of the plurality of unit regions in the display unit 260 of FIG. 1.

Although the imaging range of the imaging unit 10 is referred to as the unit region in the present embodiment as thus described, the unit region is not necessarily the imaging range of the imaging unit 10. For example, part of regions within the imaging range of the imaging unit 10 may be taken as a unit region. In this case, the unit region is smaller than the imaging range of the imaging unit 10.

Figure 3:
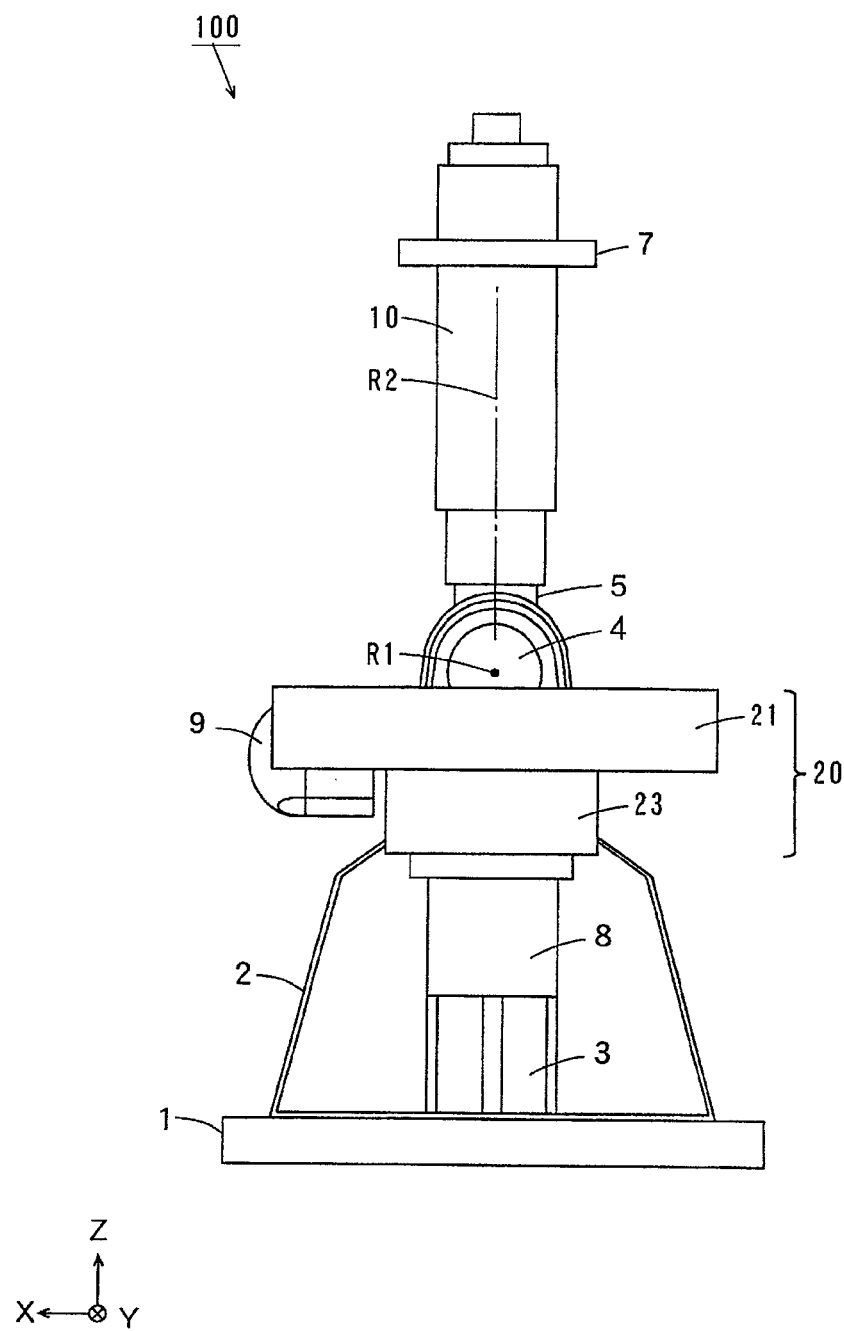
FIG. 3 is a schematic view showing a state where an imaging unit of the microscope is fixed parallel to a Z-direction.
Figure 4:
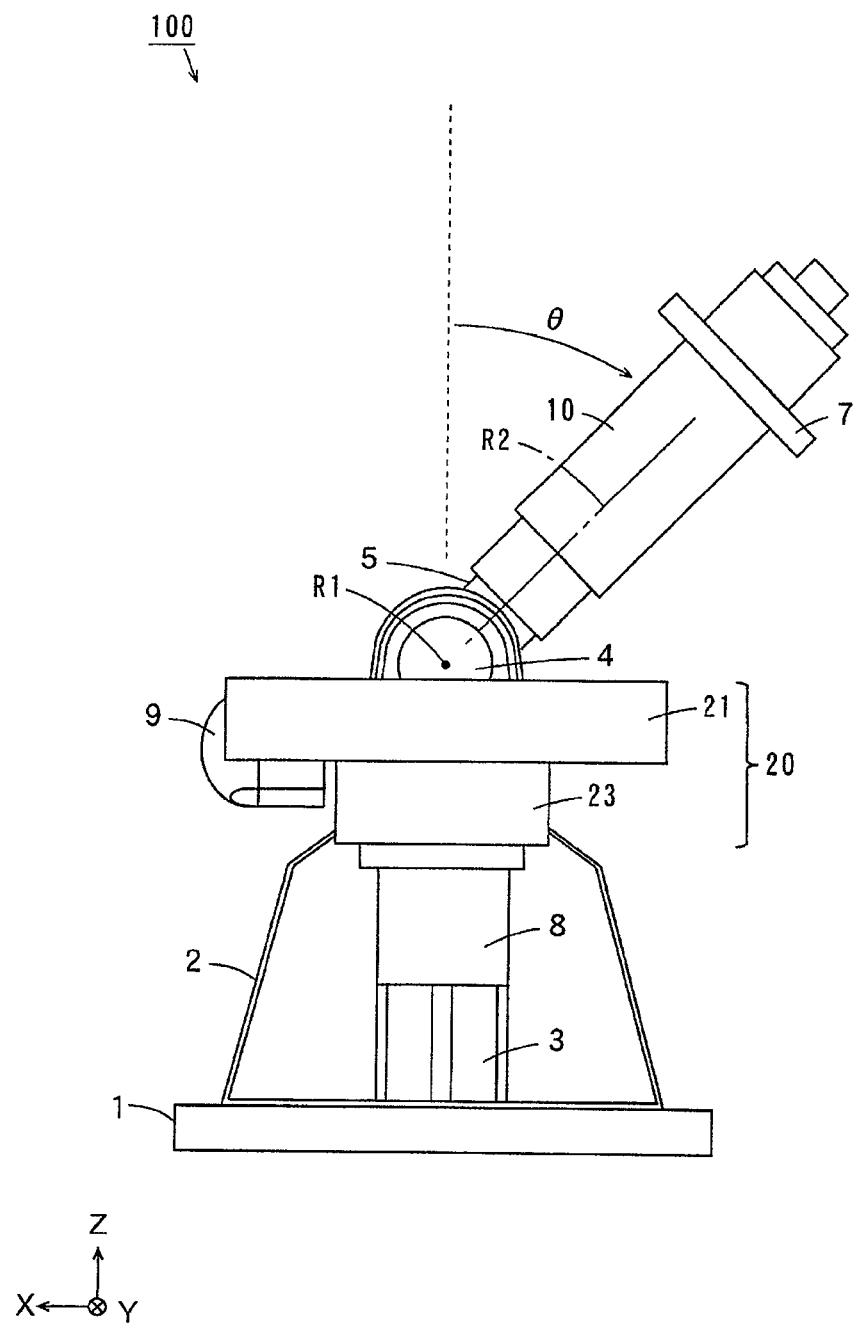
FIG. 4 is a schematic view showing a state where the imaging unit of the microscope is inclined at a desired angle from the Z-direction.

FIG. 3 is a schematic view showing a state where the imaging unit 10 of the microscope 100 is fixed parallel to the Z-direction. Further, FIG. 4 is a schematic view showing a state where the imaging unit 10 of the microscope 100 is inclined at a desired angle from the Z direction.

As shown in FIG. 3, with the rotational column 5 in a parallel state to the Z-direction, the fixing knob 9 is fastened, to fix the connecting unit 4 to the second supporting base 3. Thereby, the light axis R2 of the imaging unit 10 vertically intersects with the rotational axis R1 while being in a parallel state to the Z-direction. In this case, the light axis R2 of the imaging unit 10 is vertical to the surface of the stage 21.

The fixing knob 9 is loosened, to make the connecting unit 4 rotatable around the rotational axis R1, and the rotational column 5 inclinable with the rotational axis R1 taken as a fulcrum point. Therefore, as shown in FIG. 4, the light axis R2 of the imaging unit 10 is inclinable at an arbitrary angle θ with respect to the Z-direction. In this case, the light axis R2 of the imaging unit 10 vertically intersects with the rotational axis R1. Similarly, the light axis R2 of the imaging unit 10 is inclinable at an arbitrary angle on the side opposite to the side in FIG. 4 with respect to the Z-direction.

Therefore, a height of the surface of an observation object on the stage 21 can be made to agree with a height of the rotational axis R1, to thereby observe the same portion of the observation in a vertical direction and an oblique direction.

(2) One Display Example of Display Unit at the Time of Observation

The observation object S of FIG. 2 has a structure where three platy members of mutually different sizes are vertically laminated. The size of the platy member provided at the top is smaller than the sizes of the other two platy members. The size of the platy member provided at the center is smaller than the size of the platy member provided at the bottom. The respective top surfaces of the three platy members form a first plane S1, a second plane S2, and a third plane S3 which are parallel to the horizontal plane.

Figure 5:
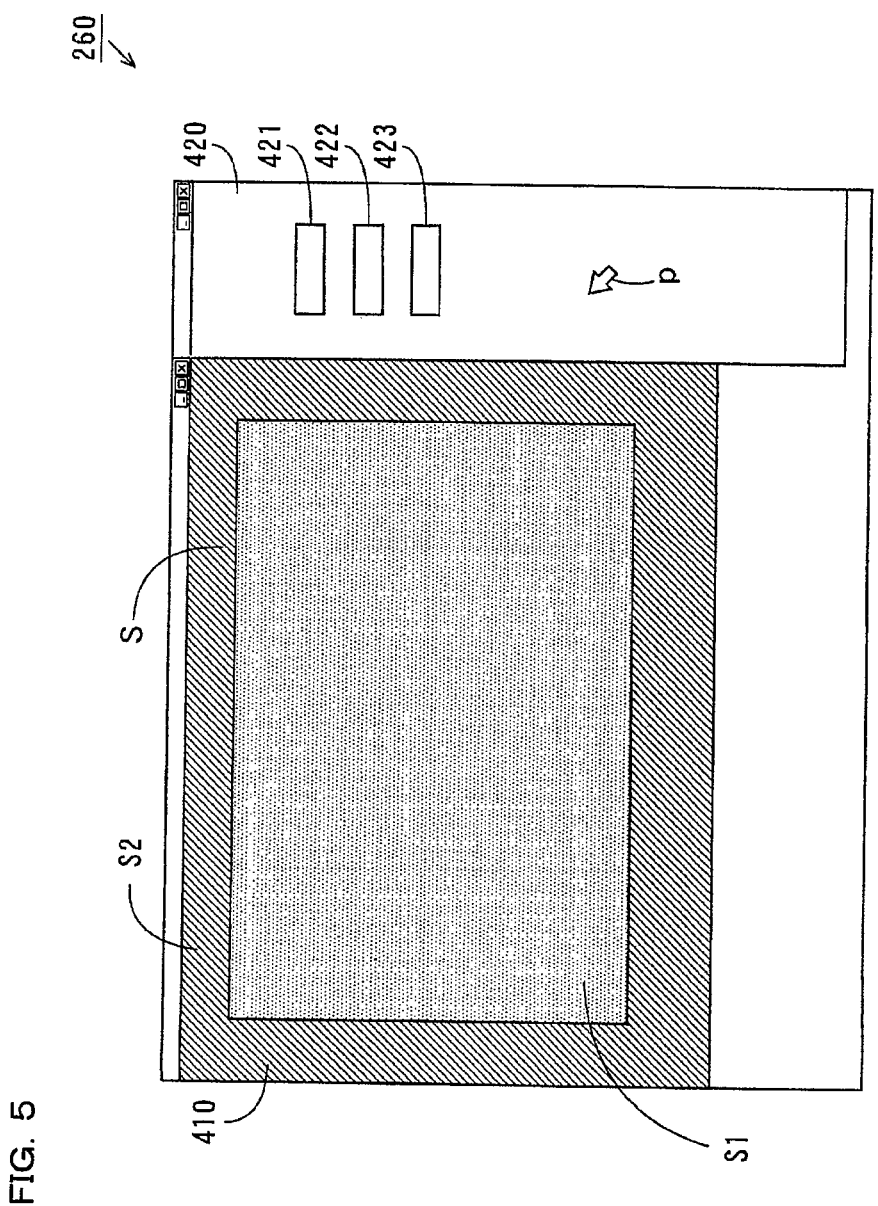
FIG. 5 is a view showing one display example of a display unit at the time when the observation object of FIG. 2 is imaged by the imaging unit of FIG. 1.

FIG. 5 is a view showing one display example of the display unit 260 at the time when the observation object S of FIG. 2 is imaged by the imaging unit 10 of FIG. 1. As shown in FIG. 5, an image display region 410, a condition setting region 420, and a pointer p are displayed on a screen of the display unit 260. At the time of imaging the observation object S by the imaging unit 10, an image based on image data is displayed in the image display region 410. In the example of FIG. 5, an image showing the first plane S1 and part of the second plane S2 of the observation object S is displayed in the image display region 410. A normal navigation button 421, a laminated navigation button 422, and an omnifocal navigation button 423 are displayed in the condition setting region 420.

In this state, the user can move the stage 21 of FIG. 2 in the x-direction or the y-direction, to thereby change the range of the images of the observation object S displayed in the image display region 410.

(3) Magnification Observation Process

As described above, in the magnification observation device 300 according to the present embodiment, the stage 21 can be moved in the x-direction and the y-direction, to thereby capture image data of a plurality of unit regions, and the image data of the plurality of unit regions can be connected, to thereby display images of the plurality of unit regions in the display unit 260 of FIG. 1. In this case, it is possible to display in the display unit 260 an image of the observation object S across a broad range exceeding one unit region.

The magnification observation process includes a navigation image generation process and a designated observation process. Hereinafter, details of the navigation image generation process and the designated observation process will be described. In the present example, before and after the magnification observation process, the magnification of the object lens 13 of FIG. 1 is constant, and a focal position of the object lens 13 (distance from the object lens 13 to a focus of the object lens 13 in a light-axis direction) is also constant.

(3-1) Navigation Image Generation Process

Figure 6A:
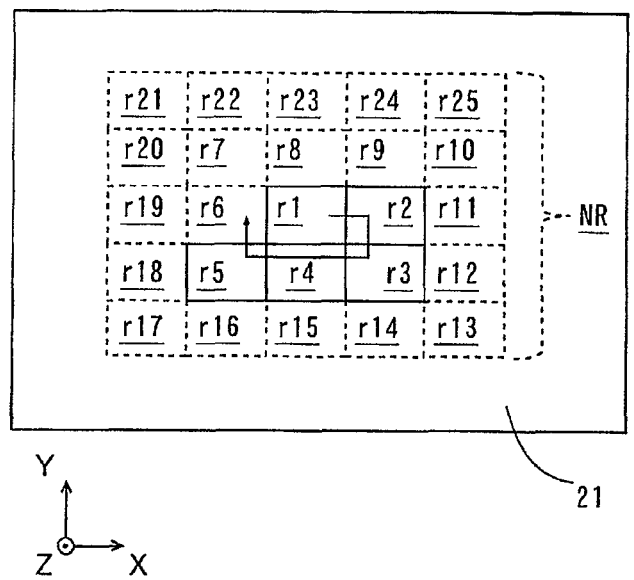
FIGS. 6A and 6B are views for describing an operation of the magnification observation device at the time of a navigation image generation process.
Figure 6B:
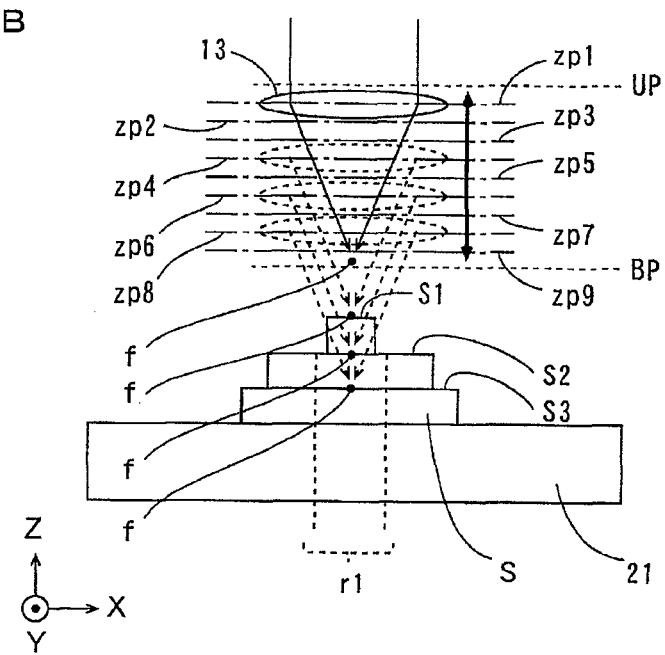

The user operates any one of the normal navigation button 421, the laminated navigation button 422, and the omnifocal navigation button 423 of FIG. 5. In response to this operation, the navigation image generation process is started. FIGS. 6A and 6B are views for describing an operation of the magnification observation device 300 at the time of the navigation image generation process.

In the case where the magnification of the object lens 13 of FIG. 1 is constant before and after the magnification observation process, the observation object S is imaged in a plurality of unit regions by starting of the navigation image generation process.

FIG. 6A is a plan view showing an imaging order at the time of the navigation image generation process. As shown in FIG. 6A, when the navigation image generation process is started, the stage 21 of FIG. 1 is moved in the x-direction and the y-direction, to sequentially image a plurality of unit regions of the observation object S within a previously set range (hereinafter, referred to as navigation region) NR which is larger than one unit region. In the present example, first to twenty-fifth unit regions r1 to r25 are sequentially imaged in a spiral form. It is to be noted that in FIG. 6A, illustration of the observation object S is omitted.

FIG. 6B is a side view showing an operation of the object lens 13 at the time of imaging the unit region r1. In the present example, an upper limit position UP and a lower limit position BP of the position in the Z-direction (hereinafter, referred to as Z position) of the object lens 13 are set in accordance with the magnification of the object lens 13. At the time of imaging each unit region in the navigation image generation process, the object lens 13 is moved between the upper limit position UP and the lower limit position BP by the lens driving unit 17 of FIG. 1. Hence, the unit region is imaged in a state where the object lens 13 is located in a plurality of Z positions. In the example of FIG. 6B, the unit region r1 is imaged in a state where the object lens 13 is located in a plurality of Z positions zp1 to zp9. In such a manner, a plurality of pieces of image data respectively corresponding to the plurality of Z positions zp1 to zp9 are captured with respect to each unit region.

At the time of imaging the observation object S by the imaging unit 10, a sampling period of image data captured by the image processing apparatus 200 is fixed. In this case, a moving speed of the object lens 13 can be adjusted, to thereby adjust respective pitches among the plurality of Z positions zp1 to zp9 of the object lens 13 at the time of imaging each unit region. Specifically, the respective pitches among the Z positions zp1 to zp9 of the object lens 13 at the time of imaging each unit region can be made larger by increasing the moving speed of the object lens 13, and the respective pitches among the Z positions zp1 to zp9 of the object lens 13 at the time of imaging each unit region can be made smaller by decreasing the moving speed of the object lens 13. In the present embodiment, each of the pitches among the Z positions zp1 to zp9 at the time of the navigation image generation process is previously set as a first pitch.

Further, at the time of imaging each unit region, data (hereinafter, referred to as shape data) showing a position of the surface of the observation object S in the Z-direction is generated based on the captured plurality of pieces of image data. The shape data is, for example, generated by the CPU 220 of FIG. 1 as follows.

As described above, the image data includes a plurality of pieces of image data. For example, a high-frequency component in a spatial distribution of values of a plurality of pieces of pixel data (electric signal levels corresponding to light receiving amounts) generated by imaging portion of a unit region in a plurality of Z positions indicates a peak at a position where a focus f of the object lens 13 is on the surface of the observation object S in part of the unit region, and decreases as the focus f of the object lens 13 gets away from the surface of the observation object S.

Thereat, based on a plurality of pieces of pixel data generated by imaging unit of the unit region at a plurality of Z positions, the CPU 220 obtains a Z position of the object lens 13 at the time when values of a plurality of pieces of image data with respect to each pixel of the color CCD 11 indicate a peak. Thereby, the CPU 220 detects the position of the surface of the observation object S in the Z-direction based on the obtained Z position of the object lens 13 and the focal position of the object lens 13, with respect to each pixel of the color CCD 11. These detection results lead to generation of the shape data.

Figure 7A:
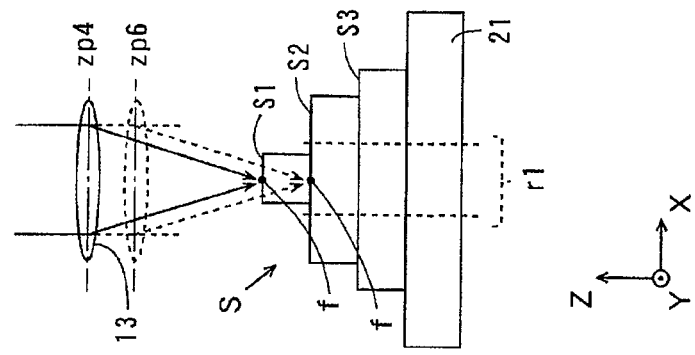
FIGS. 7A to 7C are side views for describing normal image data, laminated image data, and omnifocal image data.
Figure 7B:
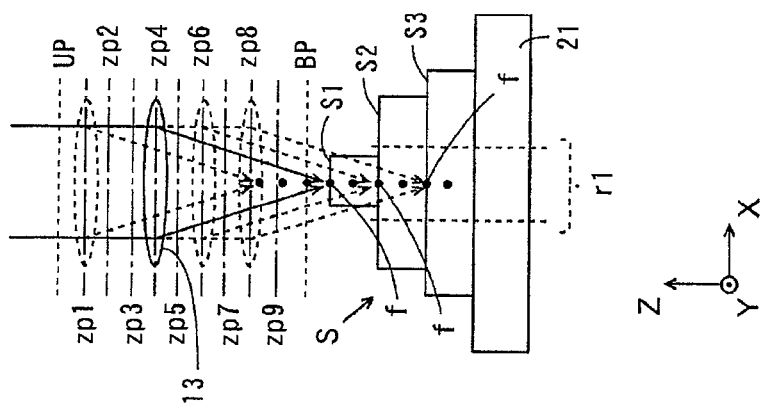
Figure 7C:
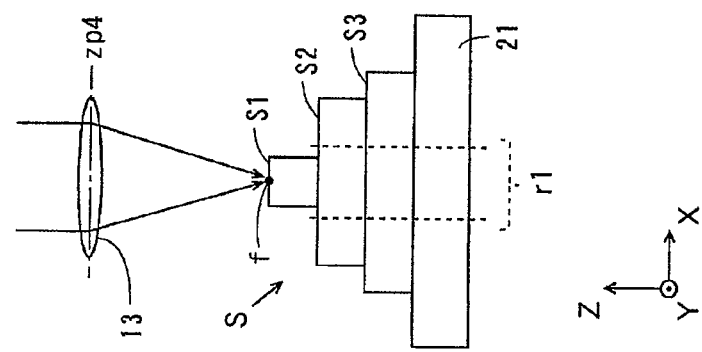

Subsequently, based on the plurality of pieces of image data captured in each unit region, any one of normal image data, laminated image data, and omnifocal image data is generated in association with each unit region. FIGS. 7A to 7C are side views for describing normal image data, laminated image data, and omnifocal image data.

The normal image data is generated at the time of the navigation image generation process when the normal navigation button 421 of FIG. 5 is operated. The normal image data is, for example, image data captured in a state where the focus f of the object lens 13 is on the surface of the observation object S in the central part of each unit region. In the example of FIG. 7A, in a state where the object lens 13 is located in the position zp4, the focus f of the object lens 13 is on the surface of the observation object S in the central part of the unit region r1. Based on the above shape data, the normal image data is generated by extracting the image data captured in the state where the focus is on the surface of the observation object S in the central part of the unit region out of the plurality of pieces of image data obtained by imaging each unit region.

The laminated image data is generated at the time of the navigation image generation process when the laminated navigation button 422 of FIG. 5 is operated. The laminated image data is an aggregate of a plurality of pieces of image data captured in a state where the object lens 13 is located in a plurality of Z positions in each unit region.

In the example of FIG. 7B, the unit region r1 is imaged in a state where the object lens 13 is located in the plurality of Z positions zp1 to zp9. In this case, laminated image data corresponding to the unit region r1 is generated based on a plurality of pieces of (nine, in the present example) image data respectively corresponding to the plurality of Z positions zp1 to zp9.

The omnifocal image data is generated at the time of the navigation image generation process when the omnifocal navigation button 423 of FIG. 5 is operated. Pixel data indicative of a peak with respect to each pixel of the color CCD 11 of FIG. 1 is extracted from a plurality of pieces of image data captured by imaging each unit region, and the extracted plurality of pieces of pixel data are synthesized, to thereby generate the omnifocal image data. According to the omnifocal image data, it is possible to generate an image focused on each of all portions in each unit region.

In the example of FIG. 7C, the first plane S1 and the second plane S2 exist whose positions in the Z-direction within the unit region r1 as the imaging object are different. The focus f of the object lens 13 is on the first plane S1 within the unit region r1 in a state where the object lens 13 is located at the Z position zp4, and the focus f of the object lens 13 is on the second plane S2 within the unit region r1 in a state where the object lens 13 is located at the Z position zp6.

In this case, in the portion of the first plane 51 out of the unit region r1, pixel data, imaged in the state where the object lens 13 is located at the Z position zp4, indicates a peak. In the portion of the second plane S2 out of the unit region r1, pixel data, imaged in the state where the object lens 13 is located at the Z position zp6, indicates a peak. A plurality of pieces of pixel data indicative of these peaks are extracted, and the extracted plurality of pieces of pixel data are synthesized. In this manner, the omnifocal image data is generated.

In the following description, the normal image data, the laminated image data, and the omnifocal image data will be collectively referred to as navigation image data.

As described above, in all the unit regions r1 to r25 within the navigation region NR of FIG. 6, a plurality of pieces of image data are captured, to generate shape data and also generate navigation image data. Thereafter, the CPU 220 of FIG. 1 connects the plurality of pieces of shape data respectively corresponding to the plurality of unit regions r1 to r25, to generate shape data corresponding to the navigation region NR. Further, the CPU 220 of FIG. 1 connects a plurality of pieces of navigation image data respectively corresponding to the plurality of unit regions r1 to r25, to generate navigation image data corresponding to the navigation region NR. Moreover, the CPU 220 stores the generated shape data and navigation image data into the storage unit 240 of FIG. 1.

Finally, the CPU 220 of FIG. 1 displays in the display unit 260 an image showing the navigation region NR (hereinafter, referred to as navigation image) based on the generated navigation image data.

Figure 8:
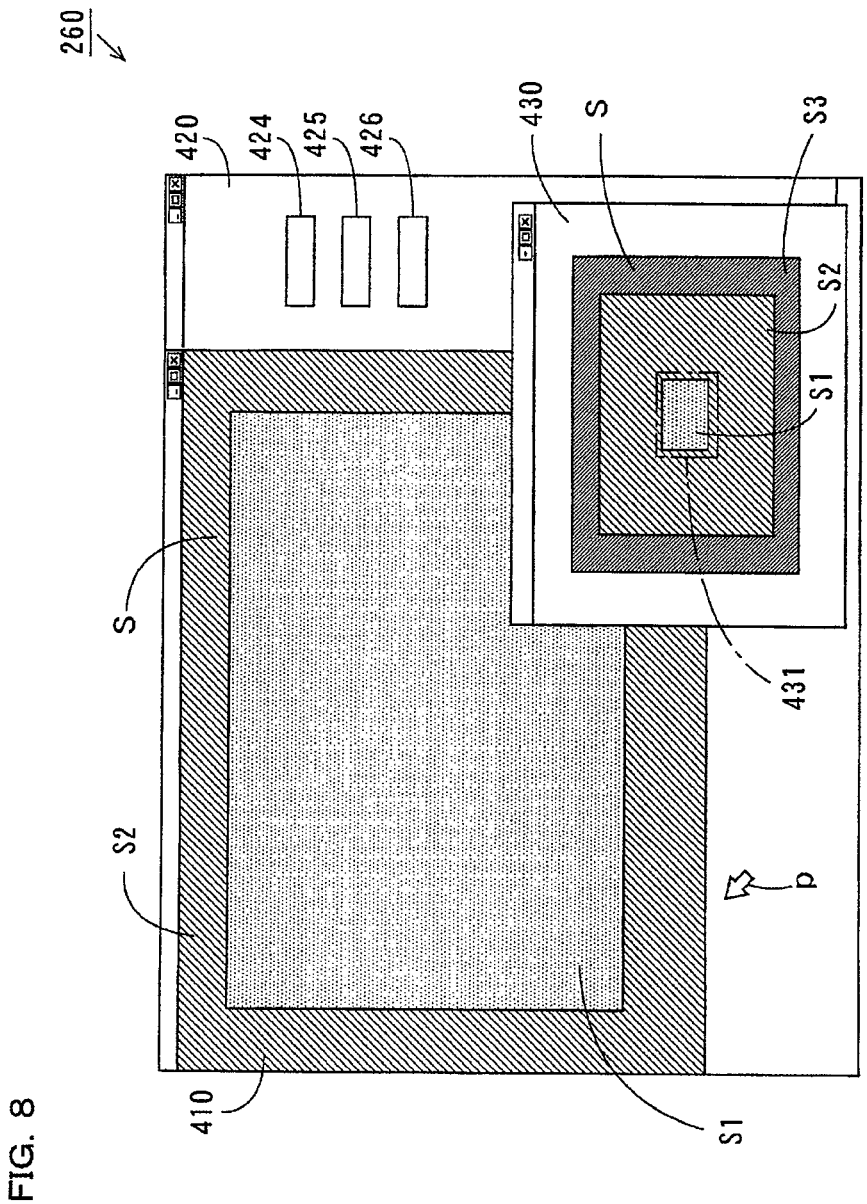
FIG. 8 is a view showing one display example of the display unit at the end of the navigation image generation process.

FIG. 8 is a view showing one display example of the display unit 260 at the end of the navigation image generation process. As shown in FIG. 8, the navigation image generation process is performed to display, in addition to the image display region 410 and the condition setting region 420 of FIG. 5, a navigation region 430 on the screen of the display unit 260.

A normal observation button 424, a detailed observation button 425, and an omnifocal observation button 426 are displayed in the condition setting region 420. Details of the normal observation button 424, the detailed observation button 425, and the omnifocal observation button 426 will be described later.

The navigation image is displayed in a navigation region 430. The unit regions displayed in the image display region 410 are represented by a frame 431 within the navigation image.

Figure 9:
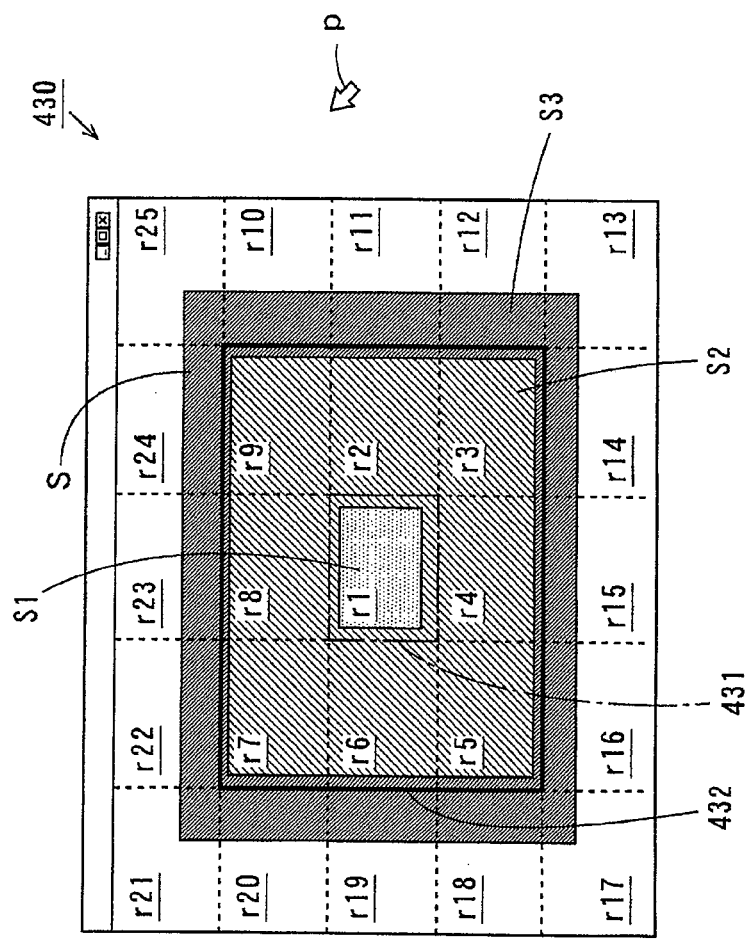
FIG. 9 is an enlarged view of a navigation region of FIG. 8.

FIG. 9 is an enlarged view of the navigation region 430 of FIG. 8. In FIG. 9, in order to facilitate understanding that a plurality of images respectively corresponding to the plurality of unit regions r1 to r25 are displayed in the display unit 260, the navigation region 430 is provided with dotted lines for partitioning the plurality of images corresponding to the plurality of unit regions r1 to r25.

Herein, when the navigation image data is the normal image data, an image of the navigation region NR, obtained by connecting a plurality of images focused on the respective central parts of the unit regions r1 to r25, is displayed as the navigation image in the navigation region 430.

At the time of display of the navigation image based on laminated image data, the user can operate the input unit 250 of FIG. 1, to thereby designate any one of the plurality of pieces of image data respectively corresponding to the plurality of Z positions zp1 to zp9. When the navigation image data is the laminated image data, any one of the plurality of pieces of image data is designated to display an image of the navigation region NR based on the designated image data as the navigation image in the navigation region 430.

When the navigation image data is the omnifocal image data, an image of the navigation region NR based on the image respectively focused on all the portions in all the unit regions r1 to r25, is displayed as the navigation image in the navigation region 430.

In such a manner as above, the navigation image is displayed in the navigation region 430 of the display unit 260 of FIG. 1, thereby completing the navigation image generation process.

(3-2) Designated Observation Process

By operation of any one of the normal observation button 424, the detailed observation button 425, and the omnifocal observation button 426 of the condition setting region 420 of FIG. 8, the designated observation process is started.

By starting the designated observation process, in the navigation region 430 of FIGS. 8 and 9, the user can designate as the observation object region one or more of the plurality of unit regions r1 to r25 displayed in the navigation image by use of the input unit 250 of FIG. 1. This facilitates the user to designate a desired observation object region of the observation object S, while viewing an image of the observation object S across a broad range exceeding one unit region.

As shown in FIG. 9, for example, part of the navigation image (unit regions r1 to r9) displayed in the navigation region 430 is designated by the user as the observation object region. In this case, the designated observation object region is represented by a frame 432 within the navigation image.

Thereafter, the CPU 220 of FIG. 1 performs a varying process according to the kind of button operated by the user. Hereinafter, there will be described processes in the case of respective operations of the normal observation button 424, the detailed observation button 425, and the omnifocal observation button 426.

When the normal observation button 424 of FIG. 8 is operated, based on the shape data stored in the storage unit 240, the CPU 220 obtains a Z position of the object lens 13 at the time when the focus f of the object lens 13 is on the surface of the observation object S in the central part of each of the unit regions r1 to r9 within the observation object region. Subsequently, the CPU 220 moves the object lens 13 to the Z position obtained with respect to each unit region, to image the observation object S. Thereby, the plurality of pieces of image data respectively corresponding to the plurality of unit regions r1 to r9 are captured. Thereafter, the captured plurality of pieces of image data are connected, and based on the connected image data, an image of the observation object region is displayed as the observation object image in the image display region 410.

Figure 10:
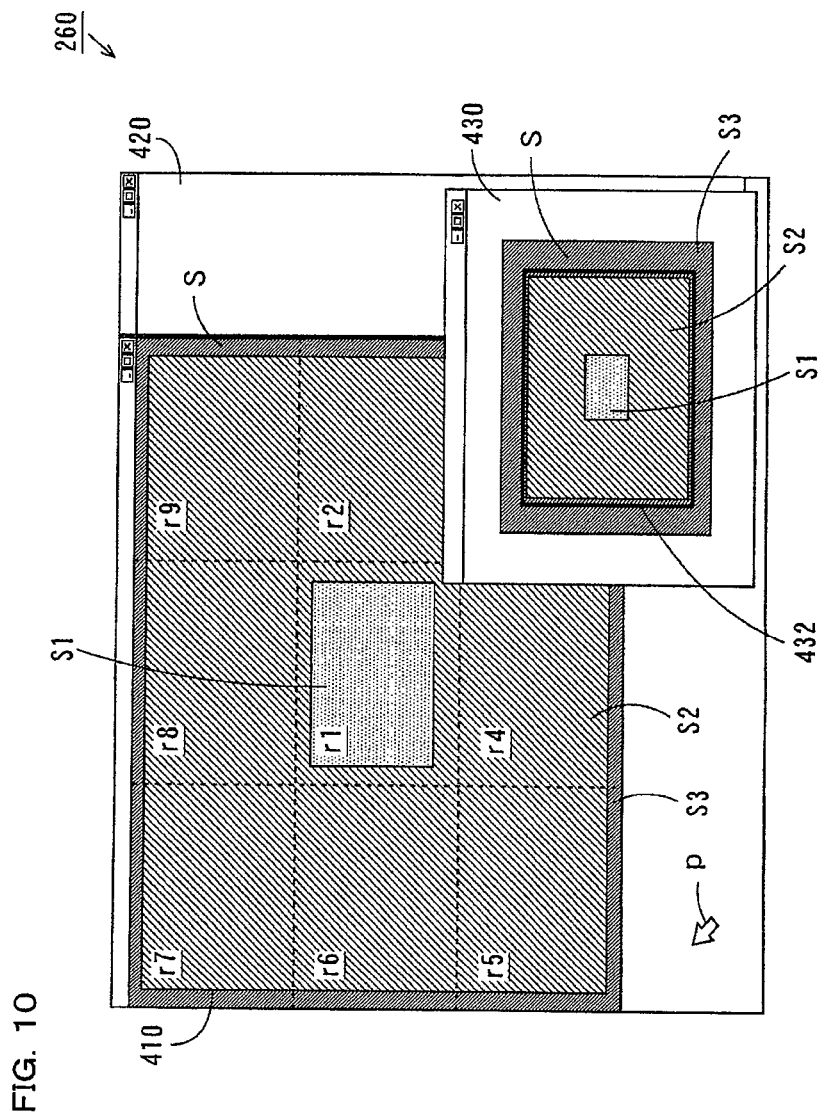
FIG. 10 is a view showing one display example of the display unit at the end of a designated observation process.

FIG. 10 is a view showing one display example of the display unit 260 at the end of the designated observation process. In the example of FIG. 10, the normal observation button 424 of FIG. 8 is operated, and by designation of the unit regions r1 to r9 as the observation object regions in the navigation image of FIG. 9, an observation object image focused on each of the central parts of the unit regions r1 to r9 is displayed in the image display region 410. It should be noted that in FIG. 10, in order to facilitate understanding that the plurality of images respectively corresponding to the plurality of unit regions r1 to r9 are displayed in the display unit 260, the image display region 410 is provided with dotted lines for partitioning the plurality of images corresponding to the plurality of unit regions r1 to r9.

When the detailed observation button 425 of FIG. 8 is operated, the Z position of the object lens 13 at the time when the focus f is on the central part of the unit region with respect to each unit region within the observation object region is searched in more detail than at the time of the navigation image generation process, and then detected. In the following description, the Z position of the object lens 13 obtained by this detection result will be referred to as a detailed focal position. Thereafter, the Z position of the object lens 13 is moved to the detailed focal position, and the unit region is imaged.

Specifically, by operation of the detailed observation button 425 of FIG. 8, based on the shape data stored in the storage unit 240, the CPU 220 obtains a Z position of the object lens 13 at the time when the focus f of the object lens 13 is on the surface of the observation object S in the central part of each of the unit regions within the observation object region.

Subsequently, the CPU 220 sets a Z-direction range (hereinafter, referred to as first Z-direction movement range) where the object lens 13 is moved for searching the detailed focal position with respect to each unit region. The first Z-direction movement range is set to a range having a fixed width centered, for example, at the Z position of the object lens 13 obtained with respect to each unit region so that the range is smaller than the range between the upper limit position UP and the lower limit position BP. In this case, with the shape data being indicative of the position of the surface of the observation object S in the Z-direction, the first Z-direction movement range is set in a short period of time.

Next, the CPU 220 images the observation object S in a plurality of Z positions while moving the object lens 13 within the set first Z-direction movement range with respect to the first unit region r1 of the observation object region. The moving speed of the object lens 13 at this time is low as compared with the moving speed of the object lens 13 at the time of the navigation image generation process. In this case, each of pitches among a plurality of Z positions of the object lens 13 corresponding to a plurality of timings to image the unit region is smaller than the first pitch described above. In such a manner, in the present embodiment, each of the pitches among the Z positions at the time of the designated observation process is previously set as a second pitch.

The CPU 220 detects a detailed focal position based on a plurality of pieces of image data obtained by imaging. Thereafter, the CPU 220 moves the object lens 13 to the detected detailed focal position, to re-image the unit region r1.

The CPU 220 repeatedly performs a process similar to the above in the subsequent unit regions (unit regions r2 to r9) of the observation object region. Thereby, a plurality of pieces of image data respectively corresponding to the plurality of unit regions r1 to r9 are captured. Finally, the plurality of pieces of image data captured with respect to each unit region are connected, and an image of the observation object region based on the connected image data is displayed as the observation object image in the image display region 410 of FIG. 10.

In the present example, with the second pitch being smaller than the first pitch, the Z position of the object lens 13 at the time when the focus f is on the central part of the unit region with respect to each unit region can be obtained in more detail. Further, the first Z-direction movement range where the object lens 13 is moved at the time of the designated observation process can be set to a sufficiently small range based on the shape data. Accordingly, even when the moving speed of the object lens 13 decreases due to the second pitch being smaller than the first pitch, an increase in time required for imaging the observation object region is suppressed.

When the omnifocal observation button 426 of FIG. 8 is operated, there is set a Z-direction range (hereinafter, referred to as second Z-direction movement range) where the object lens 13 is moved with respect to each unit region within the observation object region. In this case, since the shape data indicates the position of the surface of the observation object S in the Z-direction, the second Z-direction movement range is set in a short period of time. Thereafter, the object lens 13 moves within the second Z-direction movement range set with respect to each unit region, to image the observation object S in the plurality of Z positions.

Specifically, by operation of the omnifocal observation button 426 of FIG. 8, based on the shape data stored in the storage unit 240, the CPU 220 obtains a Z position (highest Z position) of the object lens 13 at the time when the focus f of the object lens 13 is on the surface of the observation object S at the highest position in each unit region, and a Z position (lowest Z position) of the object lens 13 at the time when the focus f of the object lens 13 is on the surface of the observation object S at the lowest position in each unit region. Further, the CPU 220 sets the second Z-direction movement range so as to include a range from the highest Z position to the lowest Z position with respect to each unit region.

Next, the CPU 220 images the observation object S in a plurality of Z positions while moving the object lens 13 within the set second Z-direction movement range with respect to the first unit region r1 of the observation object region. Similarly to the case where the detailed observation button 425 of FIG. 8 is operated, the moving speed of the object lens 13 at this time is low as compared with the moving speed of the object lens 13 at the time of the navigation image generation process.

The CPU 220 generates omnifocal image data based on a plurality of pieces of image data obtained by imaging. The CPU 220 repeatedly performs a process similar to the above in the subsequent unit regions (unit regions r2 to r9) of the observation object region. Thereby, a plurality of pieces of focal image data respectively corresponding to the plurality of unit regions r1 to r9 are captured. Finally, the captured plurality of focal image data are connected, and an image of the observation object region based on the connected focal image data is displayed as the observation object image in the image display region 410 of FIG. 10.

Also in the present example, since the second pitch is smaller than the first pitch, accuracy in observation object image sufficiently improves. Further, the second Z-direction movement range where the object lens 13 is moved at the time of the designated observation process can be set in a sufficiently small range based on the shape data. Accordingly, even when the moving speed of the object lens 13 decreases due to the second pitch being smaller than the first pitch, an increase in time required for imaging the observation object region is suppressed.

(4) Flow of Magnification Observation Process (4-1) Flow of Navigation Image Generation Process As described above, the magnification observation process according to the present embodiment includes the navigation image generation process and the designated observation process. First, a flow of the navigation image generation process will be described.

Figure 11:
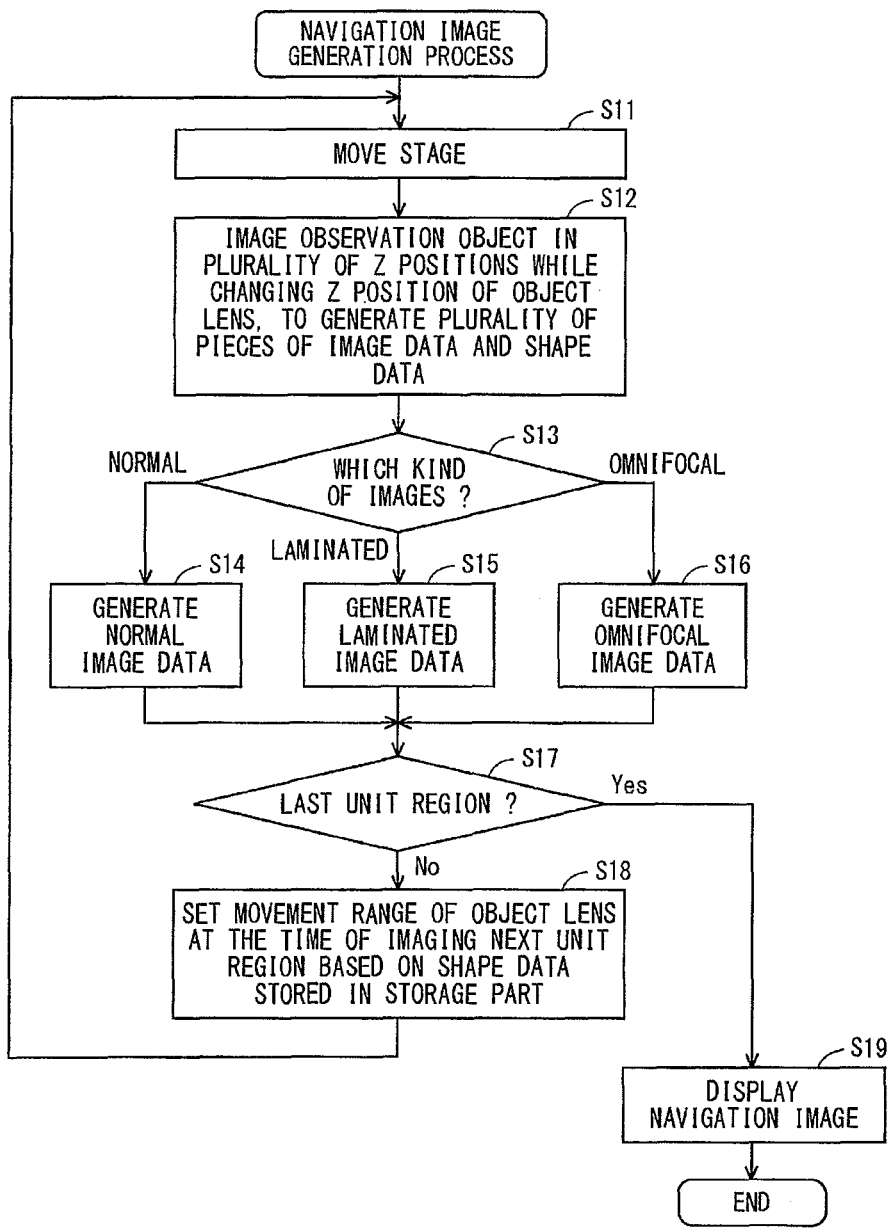
FIG. 11 is a flowchart of the navigation image generation process according to one embodiment of the present invention.

FIG. 11 is a flowchart of the navigation image generation process according to one embodiment of the present invention. The CPU 220 of FIG. 1 executes a magnification observation program stored in the storage unit 240, to perform the navigation image generation process as part of the magnification observation process according to the present embodiment.

In an initial state, a position and a size of the navigation region are previously set in accordance with the magnification of the object lens 13. In the present example, a plurality of unit regions are included in the navigation region. In this case, an imaging order of the plurality of unit regions within the navigation region is also previously set. It is to be noted that the position and the size of the navigation region and the imaging order of the plurality of unit regions may be set by the user.

In response to operation of any one of the normal navigation button 421, the laminated navigation button 422, and the omnifocal navigation button 423 of FIG. 5 by the user, the CPU 220 starts the navigation image generation process.

Upon start of the navigation image generation process, the CPU 220 moves the stage 21 so that one unit region within the navigation region is imaged in accordance with the previously set order (step S11).

Subsequently, the CPU 220 moves the object lens 13 in the Z-direction between the previously set upper limit position UP and lower limit position BP, to image the unit region at a plurality of Z positions and capture a plurality of pieces of image data, and generates shape data corresponding to the unit regions based on the captured plurality of pieces of image data (step S12). The captured plurality of pieces of image data and the generated shape data at this time are stored into the storage unit 240.

Next, based on which of the normal navigation button 421, the laminated navigation button 422, and the omnifocal navigation button 423 of FIG. 5 has been operated, the CPU 220 determines the kind of navigation image to be displayed in the navigation region 430 of FIG. 8 (step S13).

When the normal navigation button 421 of FIG. 5 is operated, the CPU 220 generates the above normal image data based on the plurality of pieces of image data captured and the shape data generated in step S12 (step S14).

On the one hand, when the laminated navigation button 422 of FIG. 5 is operated, the CPU 220 generates the above laminated image data based on the plurality of pieces of image data captured and the shape data generated in step S12 (step S15).

On the other hand, when the omnifocal navigation button 423 of FIG. 5 is operated, the CPU 220 generates the above omnifocal image data based on the plurality of pieces of image data captured and the shape data generated in step S12 (step S16).

After the process of any one of steps S14, S15, S16, the CPU 220 determines whether or not the currently-imaged unit region is a unit region to be lastly imaged within the navigation region (step S17).

When the currently-imaged unit region is not the unit region to be lastly imaged, based on the shape data corresponding to the currently-imaged unit region, the CPU 220 sets a range of the object lens 13 to be moved in the Z-direction at the time of imaging the next unit region (step S18).

For example, there is assumed a case where the mutually adjacent first unit region and second unit region are sequentially imaged. In this case, the position of the surface of the observation object S in a portion of the first unit region, which is near the second unit region, is considered almost equal to the position of the surface of the observation object S in the second unit region. Thereat, based on the shape data generated by imaging the first unit region, the position of the surface of the observation object S in the second unit region is predicted, to set the range of the object lens 13 to be moved in the Z-direction at the time of imaging the second unit region. Hence, at the time of imaging the second and subsequent unit regions, the surface of the observation object S can be imaged in a small range as compared with the previously set range between the upper limit position UP and the lower limit position BP. Consequently, the time required for the navigation image generation process can be reduced.

Subsequently, the CPU 220 returns to the process of step S11. In the second and subsequent processes of step S11, the CPU 220 moves the stage 21 so that the next unit region is imaged within the navigation region in accordance with the previously set order. Further, in the second and subsequent processes of step S12, the CPU 220 moves the object lens 13 in the Z-direction, for example, based on the movement range of the object lens 13 set by previous step S18. It should be noted that in the first process of step S12, instead of moving the object lens 13 in the Z-direction between the previously set upper limit position UP and lower limit position BP, the object lens 13 may be moved in the Z-direction within the movement range of the object lens 13 set by the user.

In step S17, when the currently-imaged unit region is the unit region to be lastly imaged, the CPU 220 connects a plurality of pieces of navigation image data (normal image data, laminated image data, or omnifocal image data) generated respectively corresponding to all the unit regions within the navigation region NR, and displays a navigation image based on the connected navigation image data in the display unit 260 of FIG. 1 (step S19). Thereby, the navigation image generation process is completed.

(4-2) Flow of Designated Observation Process

Figure 12:
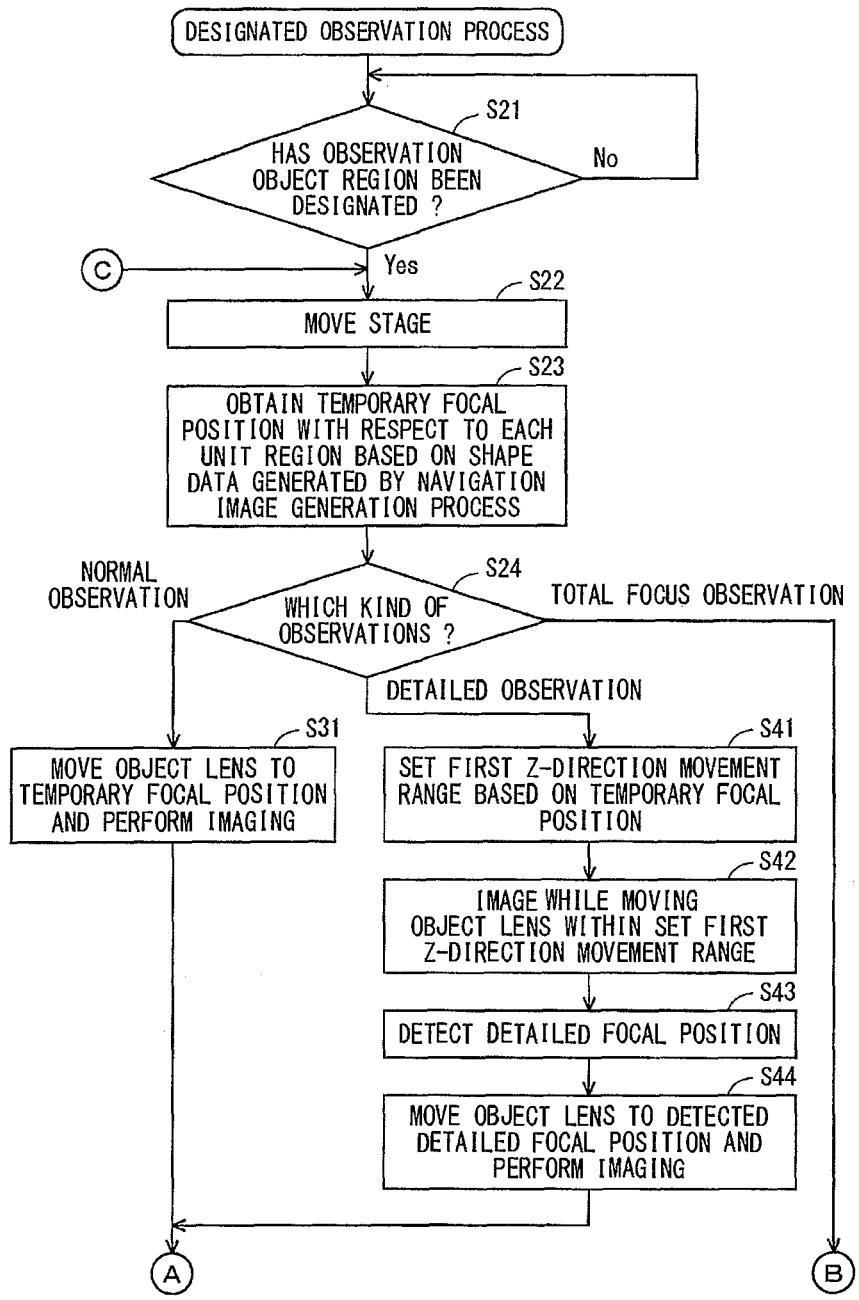
FIG. 12 is a flowchart of the designated observation process according to one embodiment of the present invention.
Figure 13:
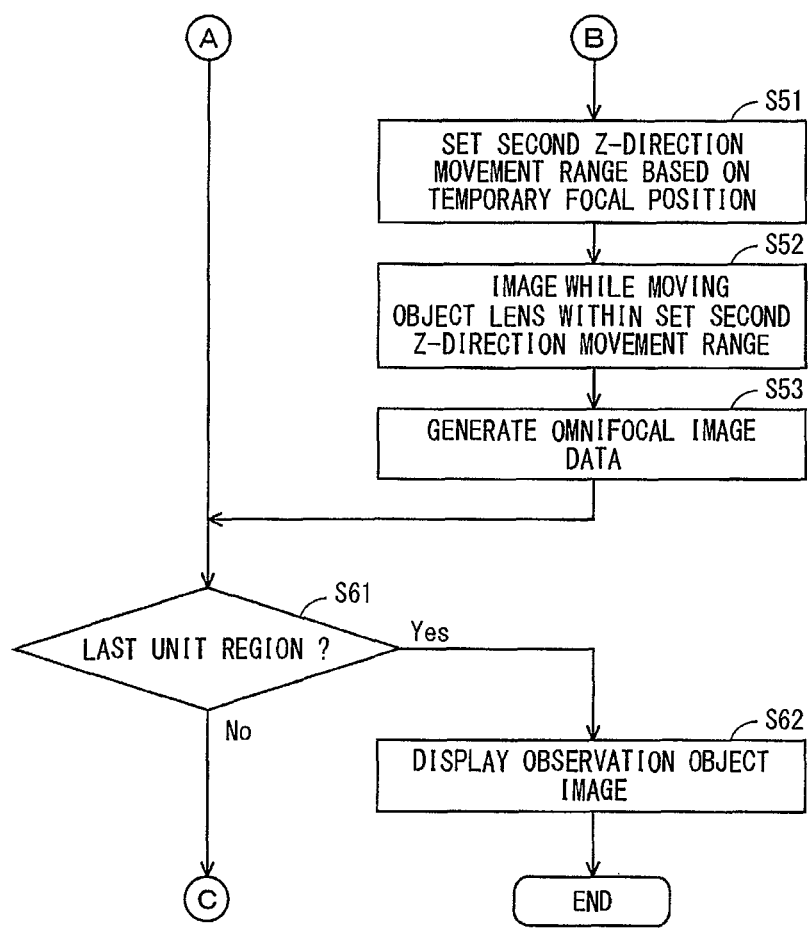
FIG. 13 is a flowchart of the designated observation process according to one embodiment of the present invention.

Subsequently, the flow of the designated observation process will be described. FIGS. 12 and 13 are flowcharts of the designated observation process according to one embodiment of the present invention. The CPU 220 of FIG. 1 executes a magnification observation program stored in the storage unit 240, to perform the designated observation process as part of the magnification observation process according to the present embodiment.

In response to operation of any one of the normal observation button 424, the detailed observation button 425, and the omnifocal observation button 426 of FIG. 8 by the user, the CPU 220 starts the designated observation process.

First, the CPU 220 determines whether or not an observation object region has been designated from the navigation image of FIG. 8 by the user (step S21). By designation of the observation object region, the CPU 220 moves the stage 21 so that one unit region within the designated observation object region is imaged (step S22).

Subsequently, the CPU 220 obtains a Z position of the object lens 13 at the time when the object lens 13 is focused on the surface of the observation object S in the central part of each of the unit regions based on the shape data generated by the navigation image generation process (step S23). In the description of the present flowchart, the Z-position of the object lens 13 obtained in step S23 will be referred to as a temporary focal position.

Next, based on which of the normal observation button 424, the detailed observation button 425, and the omnifocal observation button 426 of FIG. 8 has been operated, the CPU 220 determines the kind of observation in the designated observation process (step S24).

When the normal observation button 424 of FIG. 8 is operated, the CPU 220 moves the object lens 13 to the temporary focal position obtained in step S23, to image the unit region (step S31). Thereby, image data corresponding to the unit region is generated, and the generated image data is stored into the storage unit 240.

On the other hand, when the detailed observation button 425 of FIG. 8 is operated, the CPU 220 sets the first Z-direction movement range based on the temporary focal position obtained in step S23 (step S41). Subsequently, the CPU 220 images the unit region while moving the object lens 13 in the Z-direction within the set first Z-direction movement range (step S42). Thereby, a plurality of pieces of image data corresponding to a plurality of Z positions are generated in the unit region. Next, the CPU 220 detects the above-mentioned detailed focal position based on the generated plurality of pieces of image data (step S43). Subsequently, the CPU 220 moves the object lens 13 to the detected detailed focal position, to image the unit region (step S44). Thereby, image data corresponding to the unit region is generated, and the generated image data is stored into the storage unit 240.

On the other hand, when the omnifocal observation button 426 of FIG. 8 is operated, the CPU 220 sets the second Z-direction movement range based on the temporary focal position obtained in step S23 (step S51). Subsequently, the CPU 220 images the unit region while moving the object lens 13 in the Z-direction within the set second Z-direction movement range (step S52). Thereby, a plurality of pieces of image data corresponding to a plurality of Z positions are generated in the unit region. Next, the CPU 220 generates the above-mentioned focal image data based on the generated plurality of pieces of image data (step S53). The generated focal image data is stored into the storage unit 240.

After the process of any one of steps S31, S44, S53, the CPU 220 determines whether or not the currently-imaged unit region is a unit region to be lastly imaged within the observation object region (step S61). It is to be noted that, for example, the CPU 220 can store information indicative of the position of the unit region into the storage unit 240 at the time of storing the image data after the processes of steps S31, S44, S53 or the focal image data, to thereby perform with ease the determination process of step S61 based on the positional information.

When the currently-imaged unit region is not the unit region to be lastly imaged, the CPU 220 returns to the process of step S22. Thereby, in step S22, the stage 21 moves so that the next unit region is imaged.

On the other hand, when the currently-imaged unit region is the unit region to be lastly imaged, the CPU 220 connects a plurality of image data or omnifocal image data generated respectively corresponding to all the unit regions within the observation object region, and displays an observation object image based on the connected image data or omnifocal image data in the display unit 260 of FIG. 1 (step S62). Thereby, the designated observation process is completed.

(5) Effects (5-1) In the magnification observation device 300 according to the present embodiment, shape data is generated at the time of generating navigation image data. By designation of an observation object region based on the navigation image, an observation object region based on the shape data is imaged. In this case, since the shape data indicates the position of the surface of the observation object S in the Z-direction, the object lens 13 can be focused on the surface of the observation object S in a short period of time at the time of imaging the observation object region. This can result in reduction in time for imaging the observation object region.

(5-2) In the present embodiment, an image based on any one of the normal image data, the laminated image data, and the omnifocal image data is displayed as a navigation image.

As described above, the laminated image data is an aggregate of a plurality of pieces of image data captured in a state where the object lens 13 is located in a plurality of Z positions in each unit region. In this case, a plurality of images that are displayed based on the plurality of pieces of image data are focused on different portions or are different in focal degree. When the navigation image is displayed based on the laminated image data, an image of the navigation region NR based on image data designated by the user is displayed as a navigation image in the navigation region 430. Therefore, the user can display a desired image, out of the plurality of images being focused on different portions or different in focal degree, as the navigation image in the display unit 260. This allows the user to appropriately designate the observation object region.

Further, when the navigation image is displayed based on the omnifocal image data, in the navigation image, the focus is on each of the plurality of surfaces (first plane S1 and second plane S2 of FIG. 2) of the observation object S. This allows the user to appropriately designate the observation object region.

(6) Other Embodiments (6-1) The navigation image is used, for example, for the user to designate a desired observation object region while recognizing the entire shape of the observation object S. Therefore, the quality of the navigation image may be low as compared with the quality of the observation object image displayed in the image display region 410 by the designated observation process.

In this case, an imaging condition for the imaging unit 10 at the time of the navigation image generation process and an imaging condition for the imaging unit 10 at the time of the designated observation process can be set so as to be different from each other.

For example, the magnification of the object lens 13 at the time of the navigation image generation process is made lower than the magnification of the object lens 13 at the time of the designated observation process. In this case, the lower the magnification of the object lens 13, the larger the unit region being the imaging range of the imaging unit 10. This can reduce the number of unit regions to be imaged at the time of the navigation image generation process. Consequently, the navigation image can be displayed in a short period of time.

Further, the exposure time for the imaging unit 10 at the time of the navigation image generation process is made shorter than the exposure time for the imaging unit 10 at the time of the designated observation process. In this case, the observation object S can be imaged at high speed at the time of the navigation image generation process. Thereby, the navigation image can be displayed in a short period of time. In this case, an image remaining dark may be displayed as the navigation image. Further, a gain of the color CCD 11 may be increased, to thereby display a navigation image having inferior image quality but appropriate brightness.

Moreover, the observation object S is imaged by means of optical interferometry by use of a different imaging unit from the imaging unit 10 of FIG. 1 at the time of the navigation image generation process, and the observation object S is imaged by use of the imaging unit 10 of FIG. 1 at the time of the designated observation process. In imaging by means of optical interferometry, it is possible to acquire data on the position of the surface of the observation object S without moving the object lens. In this case, the observation object S can be imaged at high speed at the time of the navigation image generation process. Thereby, the navigation image can be displayed in a short period of time.

Further, part of a plurality of pieces of pixel data included in each image data is thinned out in acquiring a plurality of pieces of image data at the time of the navigation image generation process. In this case, an amount of data processed at the time of the navigation image generation process is reduced. Thereby, the navigation image can be displayed in a short period of time.

It is to be noted that in a confocal microscope, when the inclined surface of the observation object S is observed at a low magnification, reflected light from the surface of the observation object S can be hardly received. Further, in the confocal microscope, information on color of the surface of the observation object S cannot be obtained. Hence, in the case of observing the observation object S having the inclined surface, as the imaging condition at the time of the navigation image generation process, an imaging method by means of a normal optical microscope is preferably applied instead of an imaging method using a focal system.

Further, in a fluorescence microscope for observing the observation object S such as microorganisms, the exposure time is set long since weak fluorescence is received. Moreover, when the observation object S is irradiated with strong excitation light for generating fluorescence, the observation object S may be damaged. For this reason, in the case of observing the observation object S such as microorganisms, as the imaging condition at the time of the navigation image generation process, an imaging method by means of the normal optical microscope or an imaging method using optical interferometry is preferably applied instead of an imaging method by means of the fluorescence microscope.

(6-2) In the above embodiment, the focal position of the object lens 13 (distance from the object lens 13 to the focus of the object lens 13 in the light-axis direction) is fixed. This is not restrictive, and the object lens 13 may be a variable focal lens capable of changing a focal position. In this case, the lens driving unit 17 for moving the object lens 13 in the Z-direction becomes unnecessary.

(6-3) The image processing apparatus 200 may be configured to be capable of adjusting an imaging condition for the unit region upon start of the designated observation process. For example, at the start of the designated observation process, the image processing apparatus 200 may accept an adjustment instruction for the gain of the color CCD 11 of FIG. 1, an adjustment instruction for the exposure time, an adjustment instruction for white balance, and the like based on the user's operation on the input unit 250 of FIG. 1. In this case, the user can appropriately adjust the imaging condition at the time of the designated observation process while viewing the navigation image.

(6-4) In the above embodiment, the object lens 13 is moved in the Z-direction, to change a relative position in the Z-direction of the observation object S with respect to the object lens 13, but this is not restrictive. The stage 21 may be moved in the Z-direction, to thereby change the relative position in the Z-direction of the observation object S with respect to the object lens 13.

(7) Corresponding Relations Between Each Constitutional Element of Claims and Each Part of Embodiments Although an example of correspondence between each constitutional element of the claims and each part of the embodiments will be hereinafter described, the present invention is not limited to the following examples.

In the above embodiment, the observation object S is an example of the object, the magnification observation device 300 is an example of the magnification observation device, the stage 21 is an example of the placement unit, the normal image data, the laminated image data, the omnifocal image data, and the navigation image data are examples of the first image data, the imaging unit 10 is an example of the imaging unit, the navigation image is an example of the region presentation image, and the display unit 260 is an example of the display unit.

Further, the shape data is an example of the focus position data, the CPU 220 is an example of the processing unit and the control unit, the input unit 250 is an example of the operation unit, and the operation in the case where the normal observation button 424 of FIG. 8 is operated at the time of the designated observation process (operation of step S31 of FIG. 12), the operation in the case where the detailed observation button 425 of FIG. 8 is operated at the time of the designated observation process (operations of steps S41 to S44 of FIG. 12), and the operation in the case where the omnifocal observation button 426 of FIG. 8 is operated at the time of the designated observation process (operations of step S51 to S53 of FIG. 13) are examples of the focusing operations.

Moreover, the first Z-direction movement range and the second Z-direction movement range are examples of the position parameter, the setting operation for the first Z-direction movement range (operation of step S41 of FIG. 12) and the setting operation for the second Z-direction movement range (operation of step S51 of FIG. 13) are examples of the parameter setting operation, and the operation for moving the object lens 13 within the set first Z-direction movement range or second Z-direction movement range (operation of step S42 of FIG. 12 or step S52 of FIG. 13) is an example of the moving operation.

Further, the image data captured at the time of the designated observation process is an example of the second image data, the magnification of the object lens 13, the exposure time for the imaging unit 10, the imaging method, the number of pieces of pixel data used for the process, and the like at the time of the navigation image generation process are examples of the first imaging condition, and the magnification of the object lens 13, the exposure time for the imaging unit 10, the imaging method, the number of pieces of pixel data used for the process, and the like at the time of the designated observation process are examples of the second imaging condition.

Furthermore, the navigation image displayed in the display unit 260 based on the laminated image data is an example of the image (region presentation image) of the object based on at least part of the first image data designated by the operation unit, and the navigation image displayed in the display unit 260 based on the omnifocal image data is an example of the image (region presentation image) focused on the plurality of positions of the observation surfaces of the object.

As each constitutional element of the claims, a variety of other elements having the configuration or the function described in the claims can be employed.

The present invention is effectively applicable to a variety of magnification observation devices.

What is claimed is:

1. A magnification observation device which images an object to display an image of the object, comprising:
    a placement unit on which the object is mounted;
    an imaging unit for imaging the object mounted on the placement unit to capture a plurality of first image data;
    a processing unit for generating a plurality of focus position data indicating a position of an observation surface of the object in a light-axis direction of the imaging unit at a plurality of different positions in the direction perpendicular to the light-axis direction of the imaging unit, based on the plurality of pieces of first image data captured by the imaging unit with the focus position of the imaging unit relatively different in the light-axis direction of the imaging unit by a moving operation that moves at least one of the imaging unit and the placement unit along the light-axis direction of the imaging unit;
    a memory for storing a region presentation image based on the plurality of first image data and the plurality of focus position data associated with each other, the plurality of focus position data corresponding to a plurality of different regions within the region presentation image wherein the region presentation image is either extracted from the plurality of first image data or is synthesized from the plurality of first image data;
    a display unit for displaying the region presentation image stored in the memory;
    an operation unit for designating a specified region of a part of the region presentation image displayed by the display unit as an observation object region;
    and a control unit for moving the placement unit in the direction perpendicular to the light-axis direction of the imaging unit to a position corresponding to the observation object region designated by the operation unit, and for performing a focusing operation controlling at least one of the imaging unit and the placement unit based on the focus position data stored in the memory and included in the observation object region designated by the operation unit.

2. The magnification observation device according to claim 1, wherein the focusing operation includes
    a parameter setting operation for setting a position parameter related to positional relationship between the imaging unit and the placement unit in the light-axis direction of the imaging unit, based on the focus position data generated by the processing unit, and
    a moving operation for moving at least one of the imaging unit and the placement unit along the light-axis direction of the imaging unit based on the position parameter set by the parameter setting operation.

3. The magnification observation device according to claim 1, wherein
the operation unit is configured to allow a user to designate a plurality of unit regions as the observation object region in the region presentation image, and
the control unit is configured so as to perform the focusing operation on each of the plurality of unit regions designated by the operation unit, based on the focus position data generated by the processing unit.

4. The magnification observation device according to claim 1, wherein
the control unit further controls the imaging unit so as to capture a second image data for displaying an image of the observation object region by imaging the observation object region after the focus of the imaging unit has been on the observation surface in the observation object region by the focusing operation,
the display unit further displays an image of the observation object region based on the second image data captured by the imaging unit,
the imaging unit images an object with a first imaging condition at the case of acquiring the first image data and images an object with a second imaging condition at the case of acquiring the second image data, and
the first imaging condition and the second imaging condition is set so that the quality of an image based on the first image data is lower than that of an image based on the second image data.

5. The magnification observation device according to claim 1, wherein
the control unit further controls the imaging unit so as to sequentially image a plurality of unit regions, to thereby capture the first image data with respect to each unit region,
at the time of imaging one unit region of the plurality of unit region for acquiring the first image data, the control unit controls the processing unit so as to generate the focus position data in the one unit region in the light-axis direction of the imaging unit based on the first image data captured by imaging of the one unit region, and
at the time of imaging the one unit region and subsequent unit regions, the imaging unit captures the first image data using the focus position data generated at the time of imaging of the one unit region.

6. The magnification observation device according to claim 1, wherein
the control unit further controls at least one of the imaging unit and the placement unit so that a focus of the imaging unit is moved to a plurality of positions in the light-axis direction of the imaging unit and the object is respectively imaged at the plurality of positions, to thereby capture a plurality of pieces of first image data,
the operation unit is configured to allow a user to select at least part of the plurality of pieces of first image data captured respectively corresponding to the plurality of positions, and
the control unit displays an image of the object as a region presentation image in the display unit based on the at least part of the first image data selected by the operation unit.

7. The magnification observation device according to claim 1, wherein
the control unit further controls at least one of the imaging unit and the placement unit so that a focus of the imaging unit is moved to a plurality of positions in the light-axis direction of the imaging unit and the object is respectively imaged at the plurality of positions, to thereby capture a plurality of pieces of first image data, and displays an image focused on the plurality of positions of the observation surfaces of the object as a region presentation image in the display unit by selectively using each part of the plurality of pieces of the first image data captured.

8. An observation method using a magnification observation device which images an object to display an image of the object, comprising:
a) imaging the object mounted on a placement unit by an imaging unit to capture a plurality of pieces of first image data;
b) generating a plurality of focus position data indicating a position of an observation surface of the object in a light-axis direction of the imaging unit at a plurality of different positions in the direction perpendicular to the light-axis direction of the imaging unit, based on the plurality of first image data captured by step a), with the focus position of the imaging unit relatively different in the light-axis direction of the imaging unit by a moving operation that moves at least one of the imaging unit and the placement unit along the light-axis direction of the imaging unit;
c) storing a region presentation image based on the plurality of first image data in a memory for storing a region presentation image based on the plurality of first image data and the plurality of focus position data associated with each other, the plurality of focus position data corresponding to a plurality of different regions within the region presentation image wherein the region presentation image is either extracted from the plurality of first image data or is synthesized from the plurality of first image data;
d) displaying the region presentation image stored in the memory;
e) designating a specified region that is a part of the region presentation image displayed by step d) as an observation object region; and
f) moving the placement unit in the direction perpendicular to the light-axis direction of the imaging unit to a position corresponding to the observation object region designated by step Begin e), and performing a focusing operation controlling at least one of the imaging unit and the placement unit based on the focus position data stored in the memory and included in the observation object region designated by step e).

9. The observation method according to claim 8, wherein the focusing operation includes
a parameter setting operation for setting a position parameter related to positional relationship between the imaging unit and the placement unit in the light-axis direction of the imaging unit, based on the focus position data generated by step b), and
a moving operation for moving at least one of the imaging unit and the placement unit along the light-axis direction of the imaging unit based on the position parameter set by the parameter setting operation.

10. The observation method according to claim 8, wherein
step e) is configured to allow a user to designate a plurality of unit regions as the observation object region in the region presentation image, and
step f) is configured so as to perform the focusing operation on each of the plurality of unit regions designated by step e), based on the focus position data generated by step b).

11. The observation method according to claim 8, wherein step f) further includes controlling the imaging unit so as to capture a second image data for displaying an image of the observation object region by imaging the observation object region after the focus of the imaging unit has been on the observation surface in the observation object region by the focusing operation, step d) further includes displaying an image of the observation object region based on the second image data captured by the imaging unit, the imaging unit images an object with a first imaging condition at the case of acquiring the first image data and images an object with a second imaging condition at the case of acquiring the second image data, and the first imaging condition and the second imaging condition is set so that the quality of an image based on the first image data is lower than that of an image based on the second image data.

12. The observation method according to claim 8, wherein step f) further includes controlling the imaging unit so as to sequentially image a plurality of unit regions, to thereby capture the first image data with respect to each unit region, at the time of imaging one unit region of the plurality of unit region for acquiring the first image data, the focus position data in the one unit region in the light-axis direction of the imaging unit is generated by step b) based on the first image data captured by imaging of the one unit region, and at the time of imaging the one unit region and subsequent unit regions, the imaging unit captures the first image data using the focus position data generated at the time of imaging of the one unit region.

13. The observation method according to claim 8, wherein step f) further includes controlling at least one of the imaging unit and the placement unit so that a focus of the imaging unit is moved to a plurality of positions in the light-axis direction of the imaging unit and the object is respectively imaged at the plurality of positions, to thereby capture a plurality of first image data, step e) is configured to allow a user to select at least part of the plurality of first image data captured respectively corresponding to the plurality of positions, and an image of the object as a region presentation image is displayed by step f) based on the at least part of the first image data selected by step e).

14. The observation method according to claim 8, wherein step f) further includes controlling at least one of the imaging unit and the placement unit so that a focus of the imaging unit is moved to a plurality of positions in the light-axis direction of the imaging unit and the object is respectively imaged at the plurality of positions, to thereby capture a plurality of first image data, and displaying an image focused on the plurality of positions of the observation surfaces of the object as a region presentation image by selectively using each part of the plurality of the first image data captured.

* * * * *